United States Patent
Jeong

(10) Patent No.: US 10,610,622 B2
(45) Date of Patent: Apr. 7, 2020

(54) CLOSED SUCTION CATHETER

(71) Applicant: In Hwa Jeong, Seoul (KR)

(72) Inventor: In Hwa Jeong, Seoul (KR)

( * ) Notice: Subject to any disclaimer, the term of this patent is extended or adjusted under 35 U.S.C. 154(b) by 273 days.

(21) Appl. No.: 15/597,768

(22) Filed: May 17, 2017

(65) Prior Publication Data
US 2017/0246361 A1 Aug. 31, 2017

Related U.S. Application Data

(63) Continuation of application No. PCT/KR2015/012816, filed on Nov. 27, 2015.

(30) Foreign Application Priority Data

Dec. 31, 2014 (KR) .................... 20-2014-009690 U

(51) Int. Cl.
*A61M 1/00* (2006.01)
*A61M 16/04* (2006.01)

(52) U.S. Cl.
CPC ........ *A61M 1/0045* (2014.02); *A61M 1/0086* (2014.02); *A61M 16/0463* (2013.01); *A61M 2205/33* (2013.01); *A61M 2210/1025* (2013.01)

(58) Field of Classification Search
CPC ............ A61M 16/0463; A61M 1/0045; A61M 1/0086; A61M 2205/33; A61M 2210/1025; A61M 1/0078; A61M 1/0041
See application file for complete search history.

(56) References Cited

U.S. PATENT DOCUMENTS

| | | | | |
|---|---|---|---|---|
| 4,406,440 A | * | 9/1983 | Kulle | A61M 39/286 251/6 |
| 5,300,043 A | * | 4/1994 | Devlin | A61M 1/0043 604/250 |
| 2014/0066893 A1 | * | 3/2014 | Valentini | A61M 39/286 604/506 |

* cited by examiner

*Primary Examiner* — Kai H Weng
(74) *Attorney, Agent, or Firm* — Mintz Levin Cohn Ferris Glovsky and Popeo, P.C.; Steven M. Jensen

(57) ABSTRACT

Disclosed is a closed suction catheter for removing respiratory secretions secreted from a patient's airway, the closed suction catheter including: a tube (10) covered with a flexible outer skin (20); a suction controller (30); and a connection adaptor (40), wherein the suction controller (30) includes a main body (31) being connected to the flexible outer skin (20) by a coupling ring (32) and including: two tube holes (311 and 312) formed in the main body (31); a longitudinal groove (313) formed between the tube holes (311 and 312), with a roller (33) installed in the groove (313); a guide portion (315) formed on a side wall (314) of the groove (313); and a bottom surface (316) inclindly formed at the main body (31) with the tube (10) placed on the bottom surface (316), such that an opening ratio of the tube (10) is controlled by movement of the roller (33).

1 Claim, 4 Drawing Sheets

CLOSED SUCTION CATHETER

CROSS REFERENCE TO RELATED APPLICATION

The present application is a continuation application of International Application No. PCT/KR2015/012816 filed on Nov. 27, 2015, which claims priority to Korean Application No. 20-2014-0009690 filed on Dec. 31, 2014, which applications are incorporated herein by reference.

TECHNICAL FIELD

The present invention relates generally to a closed suction catheter for removing respiratory secretions secreted from a patient's airway. More particularly, the present invention relates to a closed suction catheter, in which a roller mounted on a main body of a suction controller moves along a longitudinal groove, and thus the suction pressure of a tube is controlled in accordance with the degree of movement of the roller moving along the longitudinal groove.

BACKGROUND ART

Korean Patent No. 10-0799028 (registered on Jan. 22, 2008) discloses "Improved closed suction catheter assembly adaptor and system containing the same".

The closed suction catheter assembly adaptor includes a housing defining an inner chamber and having a first end configured to be removably engaged to an end of an artificial airway tube, and a second end configured to communicate with an end of a closed suction catheter system, wherein the housing further includes an internal structure radially inwardly extending from the housing and defining an air passageway between the housing and the artificial airway tube, such that air is inhaled and exhaled by the breathing patient through the artificial airway to which the adaptor is attached.

The closed suction catheter is provided with a push-type suction control valve at a position opposite to the adaptor. However, the push-type suction control valve cannot control the suction pressure, and the suction pressure gradually decreases during the course of the operation and thus the suction pressure cannot be maintained uniformly.

SUMMARY

Accordingly, the present invention has been made keeping in mind the above problems occurring in the prior art, and an object of the present invention is to provide a closed suction catheter, in which the suction pressure of a tube is controlled in accordance with the degree of movement of a roller along a longitudinal groove of a main body of a suction controller by changing the structure of the suction controller, a user operates the roller with one hand and checks the suction pressure by viewing the position of the roller, and any one of irregular portions of the roller is engaged with any one of irregular portions of the main body to fix the position of the roller, such that the preset suction pressure is maintained uniformly.

In order to accomplish the above object, the present invention provides a closed suction catheter including: a tube covered with a flexible outer skin; a suction controller provided at a first end of the tube and controlling a suction pressure; and a connection adaptor provided at a second end of the tube.

The suction controller may include a main body connected to the flexible outer skin by a coupling ring, the main body including: two tube holes formed in the main body such that the tube passes through the main body; a longitudinal groove formed at a position between the two tube holes, with a roller installed in the longitudinal groove; a guide portion formed on a side wall of the longitudinal groove and guiding movement of the roller; and a bottom surface inclinedly formed at the main body with the tube placed on the bottom surface such that when the roller moves from a first end to a second end of the main body, the roller presses the tube to close the tube, and when the roller moves from the second end to the first end of the main body, the tube is opened, whereby an opening ratio of the tube is controlled by the roller provided at the main body.

The main body may include a plurality of irregular portions formed on a side portion of the longitudinal groove in a longitudinal direction in which the roller moves, the irregular portions being placed above the guide portion, and the roller includes a plurality of irregular portions circumferentially formed on a side portion of the roller, such that any one of the irregular portions of the roller is engaged with any one of the irregular portions of the main body.

As described above, in the closed suction catheter according to the present invention, it is possible to control the suction pressure of the tube in accordance with the degree of movement of the roller moving from the first end to the second end of the main body along the longitudinal groove of the main body. It is also possible to precisely control the suction force in the tube by controlling the movement of the roller relative to the length of the longitudinal groove. Further, a user can operate the roller with one hand and can check the suction pressure by viewing the position of the roller. In addition, since the tube passes through the main body and the end of the tube is directly connected to a suction machine, it is possible to maintain the suction force of the suction machine in the tube. Further, any one of the irregular portions of the roller is engaged with any one of the irregular portions of the main body such that the position of the roller is fixed, so it is possible to uniformly maintain the preset suction pressure.

DETAILED DESCRIPTION

Figure 1:
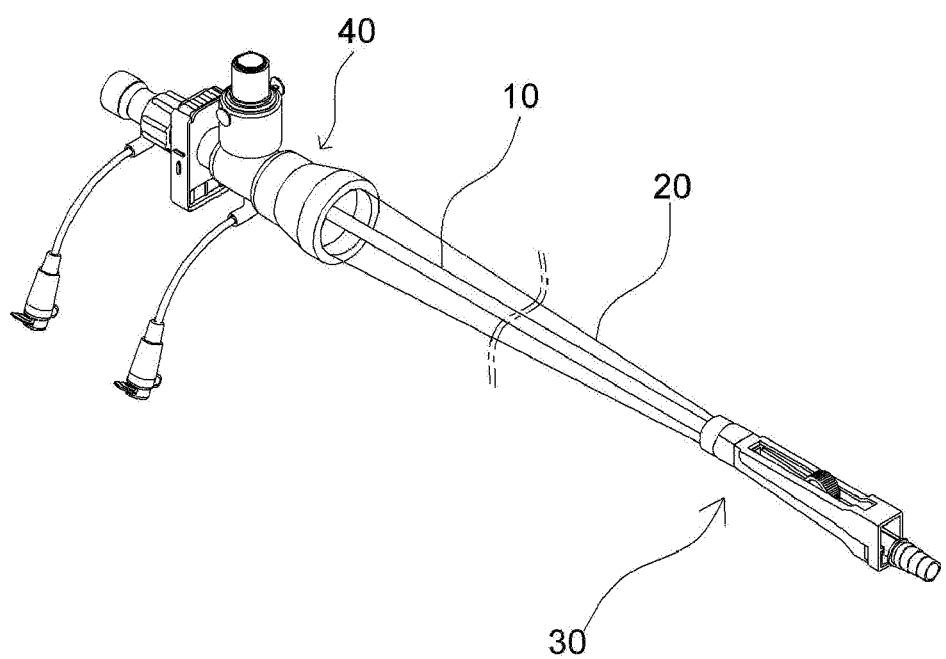
FIG. 1 is a perspective view showing a closed suction catheter according to the present invention.

Hereinafter, exemplary embodiments of the present invention will be described in detail with reference to the accompanying drawings.

Referring to FIGS. 1 to 4, a closed suction catheter according to the present invention includes a tube 10 covered with a flexible shell 20, a suction controller 30 provided at a first end of the tube 10 and controlling a suction pressure, and a connection adaptor 40 provided at a second end of the tube 10.

In the closed suction catheter as described above, the suction controller 30 includes a main body 31 connected to the flexible outer skin 20 by a coupling ring 32, the main body 31 including: two tube holes 311 and 312 formed in the main body 31 such that the tube 10 passes through the main body 31; a longitudinal groove 313 formed at a position between the two tube holes 311 and 312, with a roller 33 installed in the longitudinal groove 313; a guide portion formed on a side wall 314 of the longitudinal groove 313 and guiding movement of the roller 33; and a bottom surface 316 inclinedly formed at the main body 31 with the tube 10 placed on the bottom surface 316 such that when the roller 33 moves from a first end to a second end of the main body 31 (when the roller 33 moves from the state shown in FIG. 3 to the state shown in FIG. 4), the roller 33 presses the tube 10 to close the tube 10, and when the roller 33 moves from the second end to the first end of the main body 31, the tube 10 is opened, whereby an opening ratio of the tube 10 is controlled by the roller 33 provided at the main body 31.

Figure 2:
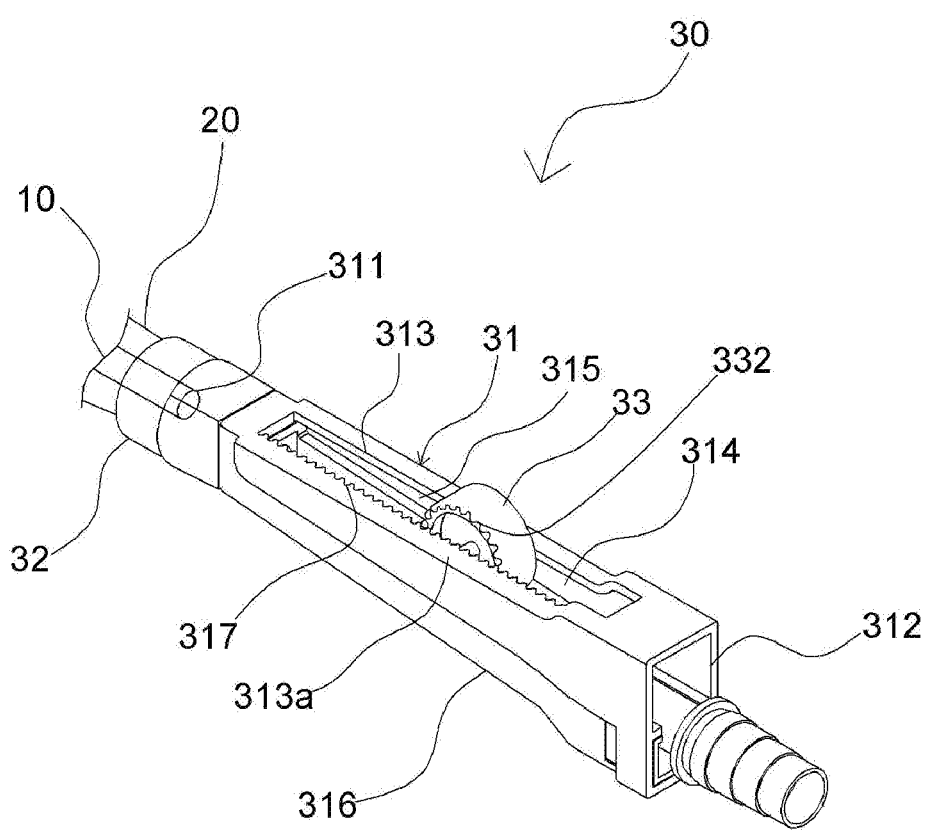
FIG. 2 is a detailed view showing a suction controller of the closed suction catheter according to the present invention.
Figure 3:
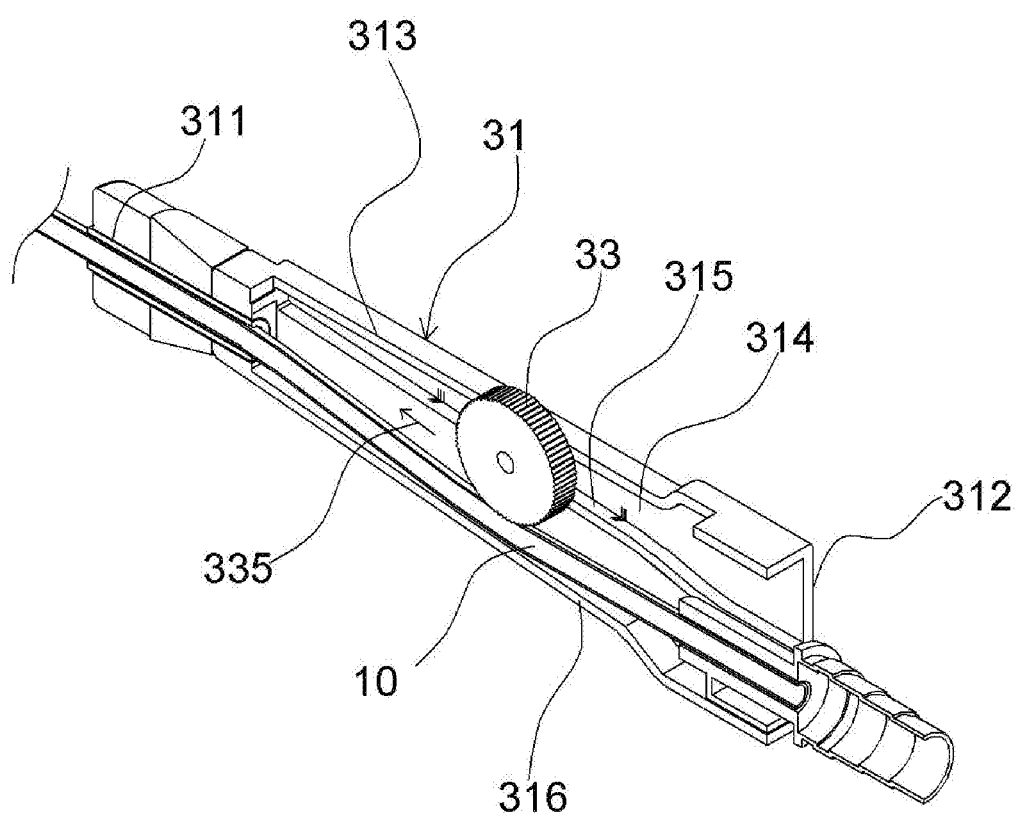
FIGS. 3 and 4 are cross-sectional views showing the suction controller of the closed suction catheter according to the present invention.
Figure 4:
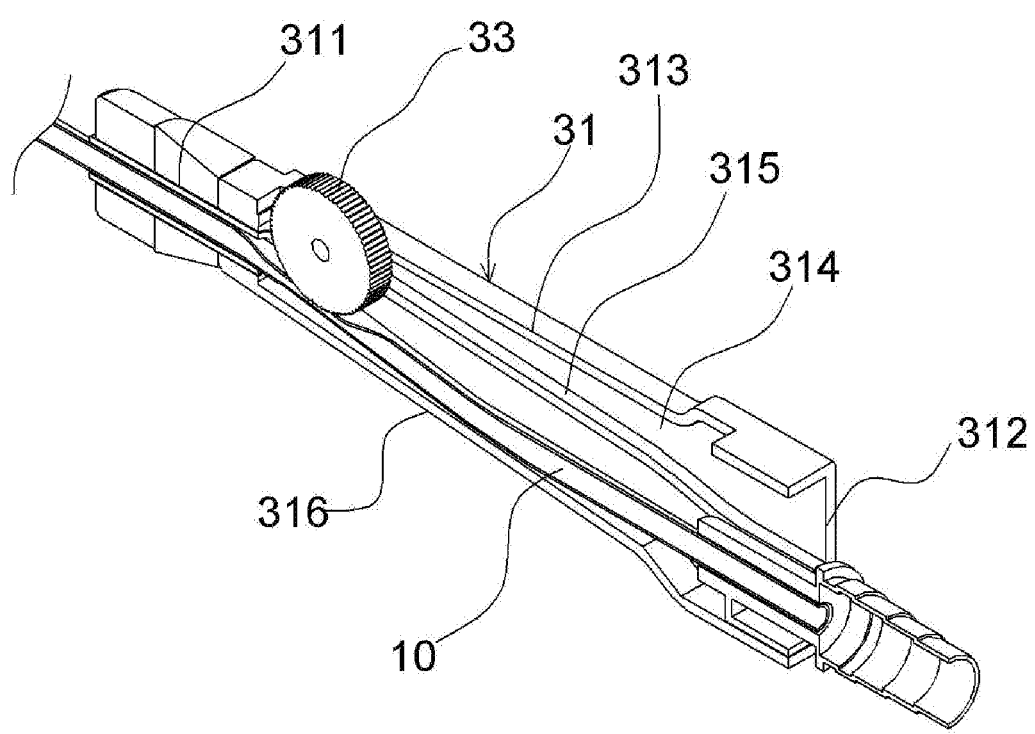

Referring to FIG. 2, the main body 31 is provided with a plurality of irregular portions 317 formed on a side portion 313a of the longitudinal groove 313 in a longitudinal direction in which the roller 33 moves, the irregular portions 317 being provided above the guide portion 315, and the roller 33 is provided with a plurality of irregular portions 332 circumferentially formed on a side portion of the roller 33, such that any one of the irregular portions 332 of the roller 33 is engaged with any one of the irregular portions 317 of the main body 31.

The closed suction catheter according to the present invention configured as described above has the following effects. A user can control the suction pressure of the tube 10 in accordance with the degree of movement of the roller 33 moving from the first end to the second end of the main body 31 (in the direction of the arrow in FIG. 3) along the longitudinal groove 313 of the main body 31. Further, it is possible to precisely control suction force in the tube 10 by lengthening a length of the longitudinal groove 313. In addition, since the tube 10 passes through the main body 31 and the end of the tube 10 is directly connected to a suction machine (not shown), suction force of the suction machine is not changed in the tube 10. Further, any one of the irregular portions 332 of the roller 33 is engaged with any one of the irregular portions 317 of the main body 31 such that the position of the roller 33 is fixed, whereby it is possible to uniformly maintain the preset suction pressure. Further, a user can operate the roller 33 with one hand and can check the suction pressure by viewing the position of the roller 33.

The invention claimed is:
1. A closed suction catheter, comprising:
a tube covered with a flexible outer skin;
a suction controller provided at a first end of the tube and controlling a suction pressure; and
a connection adaptor provided at a second end of the tube,
wherein the suction controller includes a main body connected to the flexible outer skin by a coupling ring, the main body including:
two tube holes formed in the main body such that the tube passes through the main body;
a longitudinal groove formed at a position between the two tube holes, with a roller installed in the longitudinal groove;
a guide portion formed on a side wall of the longitudinal groove to guide movement of the roller;
a bottom surface inclinedly formed at the main body with the tube placed on the bottom surface; and
a first plurality of irregular portions formed on a side portion of the longitudinal groove in a longitudinal direction in which the roller moves, the first irregular portions being placed above the guide portion, and the roller includes a second plurality of irregular portions circumferentially formed on a side portion of the roller, such that any one of the second irregular portions of the roller is engaged with any one of the first irregular portions of the main body,
wherein a width of the guide portion gradually decreases from a first end of the main body toward a second end of the main body such that when the roller moves from the first end to the second end of the main body, the roller presses the tube to close the tube, and when the roller moves from the second end to the first end of the main body, the tube is opened, whereby an opening ratio of the tube is controlled by the roller provided at the main body.

* * * * *